(12) United States Patent
Niki et al.

(10) Patent No.: US 6,657,098 B1
(45) Date of Patent: Dec. 2, 2003

(54) ABSORBENT ARTICLE

(75) Inventors: Yoshifumi Niki, Tochigi-ken (JP);
Ryuichi Noki, Tochigi-ken (JP);
Masamoto Matsukane, Tokyo (JP);
Masanobu Wakasa, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/654,054

(22) Filed: Sep. 1, 2000

(30) Foreign Application Priority Data

Sep. 1, 1999 (JP) .......................................... 11-247425

(51) Int. Cl.⁷ .................................................. A61F 13/15
(52) U.S. Cl. ......................................... 604/359; 604/367
(58) Field of Search ............................... 604/367, 359, 604/360; 424/76.1–76.7

(56) References Cited

U.S. PATENT DOCUMENTS

| | | | | |
|---|---|---|---|---|
| 3,856,014 A | * | 12/1974 | Yamauchi | 604/359 |
| 4,963,519 A | * | 10/1990 | Okabayashi et al. | 502/63 |
| 5,049,365 A | * | 9/1991 | Okabayashi et al. | 95/146 |
| 5,108,739 A | * | 4/1992 | Kurihara et al. | 424/76.1 |
| 5,407,442 A | * | 4/1995 | Karapasha | 604/359 |
| 5,630,367 A | * | 5/1997 | Kobata et al. | 110/229 |
| 5,679,316 A | * | 10/1997 | Ikenaga et al. | 423/449.7 |
| 5,690,922 A | * | 11/1997 | Mouri et al. | 424/76.1 |
| 5,733,272 A | * | 3/1998 | Brunner et al. | 604/359 |
| 5,800,806 A | * | 9/1998 | Yamamoto | 424/76.1 |
| 6,004,477 A | * | 12/1999 | Nakagawa et al. | 252/188.28 |
| 6,096,299 A | * | 8/2000 | Guarracino et al. | 424/76.1 |
| 6,287,550 B1 | * | 9/2001 | Trinh et al. | 424/76.6 |

FOREIGN PATENT DOCUMENTS

| | | |
|---|---|---|
| EP | 888785 A1 | 1/1999 |
| WO | WO9111977 | 8/1991 |
| WO | WO9526207 | 10/1995 |

\* cited by examiner

*Primary Examiner*—Weilun Lo
*Assistant Examiner*—Jacqueline Stephens
(74) *Attorney, Agent, or Firm*—Birch, Stewart, Kolasch & Birch, LLP

(57) ABSTRACT

An absorbent article 1 comprising a liquid permeable topsheet 21, a liquid impermeable backsheet 22, and a liquid retentive absorbent member 10 and containing a porous deodorizing agent, wherein the porous deodorizing agent has such pores that the volume of the pores whose diameter ranges from 20 to 200 Å is 0.2 ml/g or more, preferably 0.6 ml/g or more.

9 Claims, 2 Drawing Sheets

ABSORBENT ARTICLE

BACKGROUND OF THE INVENTION

The present invention relates to absorbent articles, such as disposable diapers, which have an excellent deodorizing effect in suppressing odor emission from excrete Absorbent articles such as disposable diapers having a deodorizing effect have been proposed, in which a deodorizing agent such as zeolite or activated carbon is used to prevent leakage of odors of excreta. However, the deodorizing performance claimed for the conventionally proposed absorbent articles is still unsatisfactory, and development of absorbent articles with more excellent deodorizing effects has been keenly demanded.

SUMMARY OF THE INVENTION

Accordingly, an object of the present invention is to provide an absorbent article which has an excellent deodorizing effect and prevents the odors of excreta from leaking out.

As a result of investigation, the present inventors have found that the above object of the present invention is accomplished by using a deodorizing agent having pores of a specific pore size in a specific ratio.

Based on the above finding, the present invention provides an absorbent article comprising a liquid permeable topsheet, a liquid impermeable backsheet (leakproof sheet), and a liquid retentive absorbent member and containing a porous deodorizing agent, wherein the porous deodorizing agent has such pores that the volume of the pores whose diameter ranges from 20 to 200 Å is 0.2 ml/g or more.

DETAILED DESCRIPTION OF THE PREFERRED EMBODIMENTS

Figure 1:
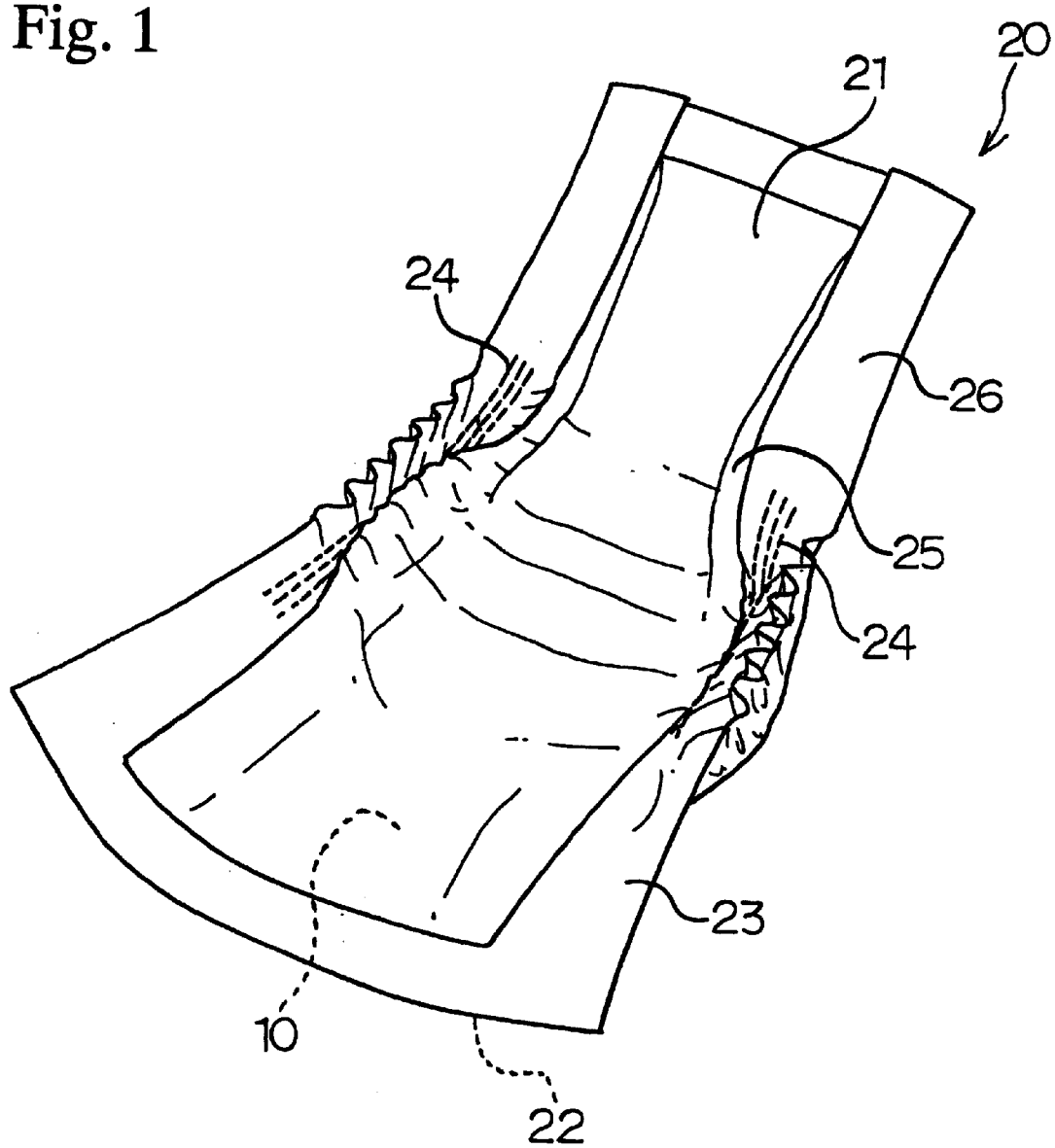
FIG. 1 is a perspective view of an example of a disposable diaper as one embodiment of the absorbent article according to the present invention.
Figure 2:
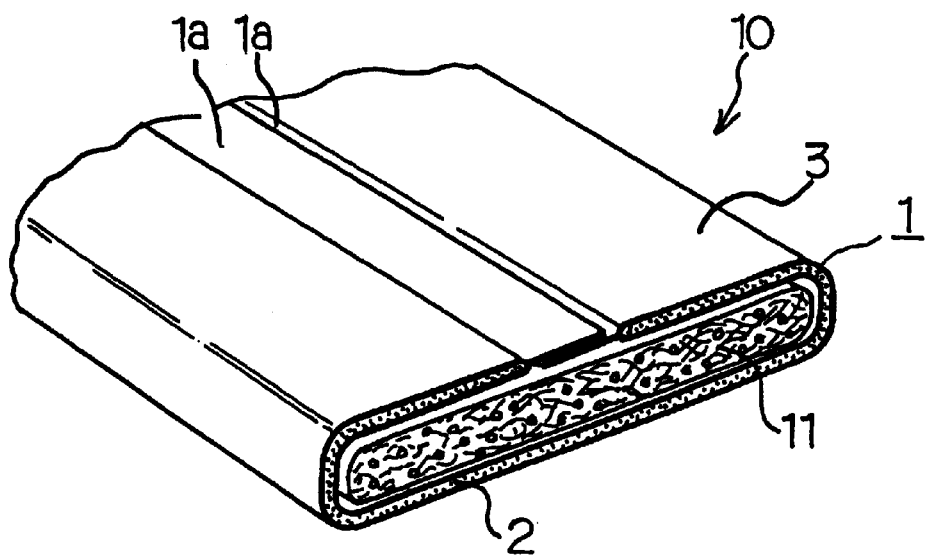
FIG. 2 is a cross-sectional view of the absorbent member used in the disposable diaper shown in FIG. 1.

The absorbent article according to the present invention will be described with particular reference to disposable diapers as a preferred embodiment thereof As shown in FIGS. 1 and 2, the disposable diaper 20 of the present invention comprises a liquid permeable topsheet 21, a liquid impermeable leakproof backsheet 22, and a liquid retentive absorbent member 10 and contains a porous deodorizing agent.

The disposable diaper 20 according to this embodiment is of the type that is put on together with underwear, waterproof pants, and the like. The absorbent member 10 is interposed between the liquid permeable topsheet 21 and the liquid impermeable backsheet 22 in the middle of the width direction of the diaper 20. A flexible side flap 23 extending outwardly in the widthwise direction of the absorbent member 10 is provided, and the crotch portion of the side flap 23 is provided with elastic member 24 along its longitudinal direction. The both longitudinal side edges in the rear side of the disposable diaper 20 are folded toward the topsheet 21 side at a slightly inner side position from the side edge of the absorbent member 10 to form the first folded portion 25. Then, the side flap 23 contained in the first folded portion 25 is folded back outward to form a second folded portion 26. The first folded portion 25 is fixedly joined to the topsheet 21, and the second folded portion 26 is fixedly joined to the first folded portion 25.

The absorbent member 10 is disposed with the middle portion of its length corresponding to the crotch portion of the disposable diaper 20 so that its function of absorbing body fluids, etc. may be performed substantially by the middle portion. The backsheet 22 has an oblong self-adhesive area (not shown) in the middle of its width, with which the disposable diaper 20 can be stuck to underwear, leakproof pants, etc. The self-adhesive area is covered with a release sheet before use.

As shown in FIG. 2, the absorbent member 10 comprises an oblong absorbent core and a laminate sheet 1 which is looped round the absorbent core 11. The both ends 1a of the laminate sheet 1 are overlapped at the middle of the width of the absorbent core 11 and adhered or fusion bonded to each other in a known manner. The absorbent core 11, except its front and rear ends thereof, is wrapped in the laminate sheet 1.

Figure 3:
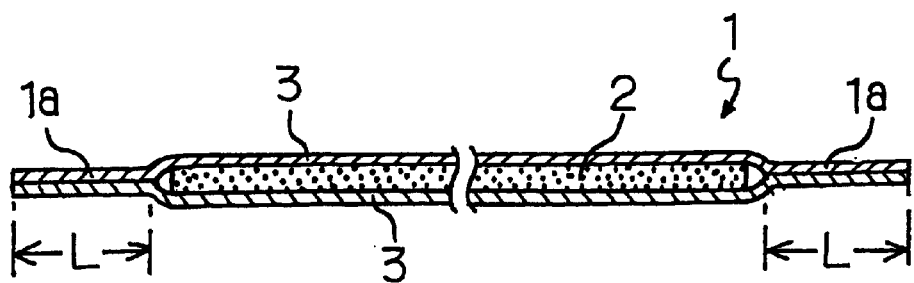
FIG. 3 is a cross-sectional view of the laminate sheet used in the absorbent member shown in FIG. 2.

As shown in FIGS. 2 and 3, the laminate sheet 1 is composed of two rectangular pulp sheets 3 of a size and a deodorizing agent-containing sheet 2 whose width is shorter than that of the pulp sheets 3 interposed between the two pulp sheets 3. In this embodiment, since the deodorizing agent-containing sheet 2 is put on the middle of the width of pulp sheets 3, the laminate sheet 1 has no deodorizing agent-containing sheet 2 at both side portions 1a thereof over the whole length. In other words, each side portion 1a is a two-ply laminate of the pulp sheets 3 adhered to each other to seal in the deodorizing agent. Thus, the deodorizing agent is prevented from falling off the laminate from its sides.

Where neither of the two side portions 1a of the laminate sheet 1 contains the deodorizing agent-containing sheet 2, whichever side portion may be superposed on top of the other, the overlap is not provided with the deodorizing agent-containing sheet 2 on its upper side. In case where one of the sides of the deodorizing agent-containing sheet 2 is substantially even with one of the sides of the laminate sheet 1, and the other side portion does not have the deodorizing agent-containing sheet 2 over the whole length, the side portion having no deodorizing agent-containing sheet is superposed on the side portion having the deodorizing agent-containing sheet 2.

The width of the side portion 1a (the length L in the cross-section shown in FIG. 3) is preferably 0.1 to 20 cm, still preferably 1 to 6 cm. With a width of 0.1 cm or greater, sealing of the deodorizing agent can be achieved. With a width of 20 cm or smaller, the deodorizing agent-containing sheet 2 can perform the function properly.

The deodorizing agent-containing sheet 2 used in the laminate sheet 1 of this embodiment is deodorizing paper made of a mixture containing a deodorizing agent and sandwiched in the pair of the pulp sheets 3 in the middle of the width of the e pulp sheets 3. The deodorizing agent-containing sheet 2 and the pulp sheets 3 are joined by successive papermaking or with an adhesive, etc.

The length of the deodorizing agent-containing sheet 2 is the same as that of the pulp sheet 3. The width of the former is smaller than that of the latter so that when the former is interposed between a pair of the latter sheets in the middle of the width, both side portions 1a of the laminate sheet 1 do not have the deodorizing agent-containing sheet 2 over the full length. The thickness of the deodorizing agent-containing sheet 2 is selected appropriately according to the use and is preferably from 0.1 to 2.0 mm, still preferably from 0.2 to 0.5 mm.

The pulp sheet 3 itself contains no deodorizing agent. With the deodorizing agent-containing sheet 2 being held between two pulp sheets 3, the laminate sheet 1 has sufficient strength, and the deodorizng agent is prevent from falling off. The thickness of the pulp sheet 3 is decided appropriately according to the use and is preferably from 0.1 to 2.0 mm, still preferably from 0.2 to 0.5 mm.

The deodorizing agent-containing sheet 2 consists mainly of a porous deodorizing agent and a fibrous material. Known natural fibers can be used as a fibrous material, such as wood pulp (e.g., NBKP or LBKP) and non-wood pulp (e.g., straw or cotton). Synthetic fiber, such as polyethylene fiber, can be used in combination in an appropriate mixing ratio to improve the sheet strength. The proportion of the fibrous material in the deodorizing agent-containing sheet 2 is preferably 50 to 99% by weight, still preferably 70 to 97% by weight. The fibrous material, being present in a proportion of 50% by weight or more, secures sufficient sheet strength and flexibility. The fibrous material being present in a proportion of 99% by weight or less exerts a sufficient deodorizing effect.

The pulp sheet 3 can be paper, nonwoven fabric, and the like. Paper as the pulp sheet 3 can be made of the same fibrous material as used in the deodorizing agent-containing sheet 2. Nonwoven fabric as the pulp sheet 3 can be any known nonwoven fabric such as spun-laced nonwoven fabric and spun-bonded nonwoven fabric.

The material making up the absorbent core 11 can include those commonly used in conventional absorbent articles, such as pulp, nonwoven fabric, and known fibrous or particulate superabsorbent polymers such as polyacrylates and starch grafted polymers.

The porous deodorizing agent which can be used in the present invention has such pores that the volume of the pores whose diameter ranges from 20 to 200 Å is 0.2 ml/g or more, preferably 0.6 ml/g. Pores having a smaller diameter than 20 Å are slow in adsorbing odor components, tending to fail to perform the deodorizing function when, for example, the deodorizing agent has a large particle size. If the volume of pores whose diameter is from 20 to 200 Å is less than 0.2 ml/g, the deodorizing agent should be used in an increased quantity, leading to an increase of cost or, in some cases, a failure of producing a sufficient deodorizing effect.

The pore diameter and the pore volume are measured in accordance with the gas adsorption method (BET method), in which a sample having been thoroughly dried by heating is evacuated and then made to adsorb nitrogen gas under pressure, and the pore diameter and the pore volume are obtained from the nitrogen gas adsorption and the equilibrium pressure to determine the pore volume distribution. "Autosorb 3" manufactured by Quantachrome Corporation was used as measuring equipment. Prior to the measurement, the equipment was treated at 100° C. for 2 hours under reduced pressure of $10^{-2}$ Torr or less.

It is desirable for at least part of the porous deodorizing agent to be hydrophobic. The language "at least part of" preferably means that at least the surface is hydrophobic. Such a porous deodorizing agent is hardly wetted with excreta and thereby prevented from lessening its deodorizing performance. It is preferred for the porous deodorizing agent to have an average particle size of 1 to 500 μm from the standpoint of fixability and dispersibility in being incorporated into an absorbent article, and texture. For securing stable deodorizing ability, the porous deodorizing agent preferably has a specific surface area of 200 to 2000 m²/g and an average pore diameter of 20 to 100 Å. A preferred pore size distribution is such that: the volume of pores whose diameter is smaller than 20 Å is 2 to 20 vol %; the volume of pores whose diameter is 20 to 200 Å is 30 to 70 vol %; and the volume of pores whose diameter is greater than 200 Å is 20 to 60 vol %, each based on the total pore volume. The pores of different sizes may be connected to each other. That is, the term "pore size distribution" as used herein is intended to denote the ratio of the volume of the parts of pores which have the above-specified respective size.

Suitable porous deodorizing agents include chemical-activated carbon, porous polymers, silica gel, zeolite, montmorillonite, and so forth. Chemical-activated carbon and porous polymers having a phenyl group are particularly preferred. The chemical-activated carbon includes zinc chloride-activated carbon and phosphoric acid-activated carbon. The porous polymer having a phenyl group includes a 2,6-diphenyl-p-phenylene oxide-based polymer and a divinylbenzene-styrene copolymer.

In order for the porous deodorizing agent to manifest sufficient deodorizing effects, it is preferably used in such an amount that the volume of pores having a diameter of 20 to 200 Å amounts to 0.3 ml or more, preferably 0.6 ml or more, per 100 g of the saturation absorption of the absorbent article. The saturation absorption of the absorbent article can be determined as follows. The absorbent article is immersed in physiological saline for 30 minutes and then drained for 30 minutes. The difference between the weight (g) after drainage and the weight (g) before immersion is taken as a saturation absorption.

The disposable diaper 20 can be used for babies, adults or persons suffering from urinary incontinence as with conventional disposable diapers. Containing the above-described specific porous deodorizing agent, the disposable diaper according to the above-described embodiment exhibits higher deodorizing effects than with conventional ones probably for the following reasons. While body fluids discharged from a human body generally emit smells, such compounds as represented by steroids amongst various odor components have relatively large molecular weights and are therefore bulky and also interact with other compounds in the excrete Therefore conventional deodorizing agents such as activated carbon whose pore size is less than 20 Å have failed to adsorb these compounds. It is considered that such bulky compounds can be adsorbed quickly by pores in a mesopore range of from 20 to 200 Å as in the porous deodorizing agent used in the present invention.

Further, the absorbent article having the above-described structure can have excreta such as body fluids absorbed and retained in its crotch portion while removing the smell of the excreta by the action of the porous deodorizing agent. While the discharged body fluids are absorbed by the longitudinally central portion of the absorbent member 10, since the deodorizing agent-containing sheet 2 of the absorbent article 10, except its front and rear ends, is covered with the pulp sheet 3, the porous deodorizing agent is prevented from running out of the absorbent member 10 together with the absorbed body fluids and therefore prevented from soiling the body or the clothes.

While the method of making the laminate sheet used in the above embodiment is not particularly restricted, a preferred method of making is described below.

Method of Making the Laminate Sheet Used in This Embodiment

A deodorizing agent-containing sheet 2 is obtained by forming a slurry containing a porous deodorizing agent and a fibrous material into a web by a usual wet papermaking process. The slurry can contain various binders for binding the porous deodorizing agent to the web as well as various additives customarily employed in papermaking. A deodorizing agent-containing sheet 2 can also be prepared by forming a slurry comprising the fibrous material and necessary additives into a web and impregnating the web with a dispersion of the porous deodorizing agent and a binder.

A pulp sheet 3 is obtained by forming a slurry mainly comprising a fibrous material into a web in the same manner as for the deodorizing agent-containing sheet 2.

The deodorizing agent-containing sheet 2 and the pulp sheet 3 are joined by successive papermaking on a papermaking machine or by means of a laminator and an adhesive, etc. in a usual manner to form a laminate having the deodorizing agent-containing sheet 2 between a pair of the pulp sheets 3. The laminate is trimmed to obtain the laminate sheet 1 with a desired width. Since the deodorizing agent-containing sheet 2 is not present in both the side portions 1a, the porous deodorizing agent is prevented from falling off and soiling the product or the production line.

Although the front and the rear ends of the deodorizing agent-containing sheet 2 in the absorbent member 10 of the absorbent article 20 are not covered with the pulp sheets 3, the absorbed body fluids, etc. stays in the central portion of the longitudinal direction without reaching the front and the rear ends. Therefore, the porous deodorizing agent does not ooze out of the ends of the laminate sheet together with the body fluids, etc.

The absorbent article of the present invention is not limited to the above-mentioned embodiment and is subject to various changes and modifications within the scope of the present invention. For example, as briefly referred to above, the entire periphery of the laminate sheet including the side portions does not always need to have no deodorizing agent-containing sheet, provided that either one of the side portions of the laminate sheet has no deodorizing agent-containing sheet over the whole length. Further, the laminate sheet does not always need to have the deodorizing agent-containing sheet over its whole width.

The absorbent member used in the absorbent article of the present invention can have various shapes and sizes according to the use.

Application of the absorbent article of the present invention is not limited to the disposable diaper of the above-described embodiment and can include disposable diapers of unfolded type or pants type, incontinence pads, sanitary napkins, and panty liners.

While the porous deodorizing agent is preferably contained in the absorbent member as illustrated above, the state of the deodorizing agent's being present is not limited thereto. For example, it may be admixed with pulp fiber used in the absorbent core 11 or it may be sandwiched in between a pair of sheets prepared from pulp fiber. In addition, the porous deodorizing agent may be held in other members constituting the diaper than the absorbent member and may be contained in portions other than the absorbent member.

EXAMPLES 1 TO 3 AND COMPARATIVE EXAMPLES 1 TO 5

The porous deodorizing agents shown in Table 1 below were tested as follows to evaluate their deodorizing function. The results obtained are shown in Table 2 below.

Test Method

Each deodorizing agent weighing 0.1 g, 1.0 g of an absorbent polymer (Aquaric CA, available from Nippon Shokubai Kagaku Kogyo Co., Ltd.), and 10 g of human urine were mixed in a weighing bottle having a diameter of 50 mm. Five testers were asked to smell the mixture and to rate the smell on a zero-to-five scale. The given scores were added up and averaged. The urine used in every tests was of the same sample.

Scale of Evaluation

5 The mixture smelled very strongly.
4 The mixture smelled strongly.
3 The mixture smelled (no change from the smell of the tested urine).
2 The smell was reduced.
1 The smell was greatly reduced (the smell was hardly recognizable as that of urine).
0 The mixture was odorless.

TABLE 1

| | Deodorizing Agent | Average Particle Size ($\mu$m) | Specific Surface Area ($m^2/g$) | Pore Volume (ml/g) | |
|---|---|---|---|---|---|
| | | | | <20 Å | 20–200 Å |
| Example 1 | zinc chloride-activated carbon | 17 | 1300 | 0.07 | 1.00 |
| Example 2 | zinc chloride-activated carbon | 250 | 1050 | 0.05 | 0.85 |
| Example 3 | divinylbenzene-styrene copolymer | 100 | 520 | 0.10 | 0.30 |
| Compara. Example 1 | coconut shell active carbon (steam-activated) | 250 | 1050 | 0.13 | 0.08 |
| Compara. Example 2 | silica gel | 50 | 450 | 0.08 | 0.18 |
| Compara. Example 3 | amorphous zeolite | <5 | 29 | 0.002 | 0.04 |
| Compara. Example 4 | acid clay | <5 | 80 | 0.003 | 0.12 |
| Compara. Example 5 | sepiolite | <5 | 180 | 0.02 | 0.18 |

TABLE 2

| | Deodorizing Agent | Smell after 30 mins. |
|---|---|---|
| Example 1 | zinc chloride-activated carbon | 0.3 |
| Example 2 | zinc chloride-activated carbon | 0.5 |
| Example 3 | divinylbenzene-styrene copolymer | 1.0 |
| Compara. Example 1 | coconut shell active carbon (steam-activated) | 1.8 |
| Compara. Example 2 | silica gel | 1.6 |
| Compara. Example 3 | amorphous zeolite | 2.5 |
| Compara. Example 4 | acid clay | 2.0 |
| Compara. Example 5 | sepiolite | 2.0 |

As can be seen from the results in Table 2, the deodorizing agents of Examples 1 to 3, which are the deodorizing agents used in the present invention, exhibit excellent deodorizing effects, whereas those of Comparative Examples 1 to 5 were unable to reduce the smell to the degree unrecognizable as urine.

As illustrated above in detail, the absorbent article according to the present invention has a high deodorizing effect, managing to prevent leakage of the odor of excreta.

What is claimed is:

1. An absorbent article comprising a liquid permeable topsheet, a liquid impermeable backsheet, and a liquid retentive absorbent member and containing a porous deodorizing agent, wherein said porous deodorizing agent has such pores that the volume of said pores whose diameter ranges from 20 to 200 Å is e0.2 ml/g or more, and wherein the volume of said pores whose diameter is smaller than 20 Å is 2 to 20 vol%, the volume of said pores whose diameter is 20–200 Å is 30–70 vol% and the volume of said pores whose diameter is greater than 200 Å is 20–60 vol %.

2. An absorbent article according to claim 1, wherein said porous deodorizing agent is zinc chloride-activated carbon.

3. An absorbent article according to claim 1, wherein the total volume of said pores whose diameter ranges from 20 to 200 Å is 0.3 ml or more per 100 g of the saturation absorption of said absorbent article.

4. An absorbent article according to claim 1, wherein said absorbent member includes a laminate sheet comprising two pulp sheets and a deodorizing agent-containing sheet which is interposed between said pulp sheets and contains said porous deodorizing agent, said laminate sheet not being provided with said deodorizing agent-containing sheet at least on one side portion thereof over the whole length.

5. An absorbent article according to claim 1, wherein said porous deodorizing agent has a specific surface area of 520 to 2000 m$^2$/g.

6. An absorbent article according to claim 5, wherein said deodorizing agent has a specific surface area of 520 to 1300 m$^2$/g.

7. An absorbent article comprising a liquid permeable topsheet, a liquid impermeable backsheet, and a liquid retentive absorbent member and containing a porous deodorizing agent, wherein said porous deodorizing agent has such pores that the volume of said pores whose diameter ranges from 20 to 200 Å is 0.2 ml/g or more, wherein the volume of said pores whose diameter is smaller than 20 Å is 2 to 20 vol %, the volume of said pores whose diameter is 20–200 Å is 30–70 vol% and the volume of said pores whose diameter is greater than 200 Å is 20–60 vol %, and wherein said porous deodorizing agent has a specific surface area of 520 to 2000 m$^2$/g.

8. An absorbent article comprising a liquid permeable topsheet, a liquid impermeable backsheet, and a liquid retentive absorbent member, wherein said liquid retentive absorbent member comprises a laminate sheet comprising two pulp sheets and a porous deodorizing agent which is interposed between said pulp sheets, and wherein a portion of an absorbent core is wrapped in said laminate sheet, wherein said porous deodorizing agent has such pores that the volume of said pores whose diameter ranges from 20 to 200 Å is 0.2 ml/g or more.

9. An absorbent article according to claim 8, wherein said porous deodorizing agent has a specific surface area of 520 to 2000 m$^2$/g.

* * * * *